(12) United States Patent
Van Beek

(10) Patent No.: US 12,042,172 B2
(45) Date of Patent: Jul. 23, 2024

(54) MEDICAL IMPLANT DELIVERY DEVICE

(71) Applicant: Valens Recovery Solutions LLC, Edina, MN (US)

(72) Inventor: Allen L. Van Beek, Minneapolis, MN (US)

(73) Assignee: VALENS RECOVERY SOLUTIONS LLC, Edina, MN (US)

( * ) Notice: Subject to any disclaimer, the term of this patent is extended or adjusted under 35 U.S.C. 154(b) by 1055 days.

(21) Appl. No.: 16/920,564

(22) Filed: Jul. 3, 2020

(65) Prior Publication Data

US 2021/0000504 A1 Jan. 7, 2021

Related U.S. Application Data

(60) Provisional application No. 62/870,433, filed on Jul. 3, 2019.

(51) Int. Cl.
| | | |
|---|---|---|
| *A61B 17/34* | (2006.01) | |
| *A61B 17/00* | (2006.01) | |
| *A61B 90/00* | (2016.01) | |
| *A61K 31/105* | (2006.01) | |

(52) U.S. Cl.
CPC .... *A61B 17/3468* (2013.01); *A61B 17/00234* (2013.01); *A61B 90/361* (2016.02); *A61B 90/39* (2016.02); *A61K 31/105* (2013.01); *A61B 2017/00221* (2013.01); *A61B 2017/0046* (2013.01); *A61B 2090/373* (2016.02); *A61B 2090/395* (2016.02)

(58) Field of Classification Search
CPC ........ A61B 17/3468; A61B 2017/0046; A61B 2090/373; A61B 2090/395; A61B 90/30; A61B 90/39; A61M 37/0069
See application file for complete search history.

(56) References Cited

U.S. PATENT DOCUMENTS

| | | |
|---|---|---|
| 5,441,041 A | 8/1995 | Sauer et al. |
| 6,248,112 B1 | 7/2001 | Gambale et al. |
| 6,648,819 B2 | 11/2003 | Tenhuisen et al. |
| 7,427,415 B2 | 9/2008 | Scharp et al. |
| (Continued) | | |

OTHER PUBLICATIONS

Sezgin et al., Disulfiram Implantation for the Treatment of Alcoholism: Clinical Experiences from the Plastic Surgeon's Point of View, Archives of Plastic Surgery 2014;41(5):571-575. (Year: 2014).*

(Continued)

*Primary Examiner* — Deanna K Hall
(74) *Attorney, Agent, or Firm* — GRUMBLES LAW PLLC; Brittany Haanan

(57) ABSTRACT

The medical implant delivery device comprises a handheld assembly and an obturator. The handheld assembly can include an elongated shaft defining a chamber having a distal end and a proximal end, and an imaging device secured within the chamber adjacent to the distal end. The imaging device can comprise a light source and a lens. The obturator can include an elongated member having a light transmitting member and a plunger, wherein the obturator may be slidably disposed in a first position such that at least a portion of the elongated member may be within the chamber and the light transmitting member may be optically coupled to the light source and the lens.

18 Claims, 9 Drawing Sheets

(56) References Cited

U.S. PATENT DOCUMENTS

| | | | |
|---|---|---|---|
| 7,741,273 | B2 | 6/2010 | McKay |
| 7,736,330 | B2 | 7/2010 | Bardy |
| 7,850,639 | B2 | 12/2010 | Rue et al. |
| 7,909,836 | B2 | 3/2011 | McLean et al. |
| 8,147,511 | B2 | 4/2012 | Perry et al. |
| 8,192,353 | B2 | 6/2012 | Smith |
| 8,211,087 | B2 * | 7/2012 | Carter ............... A61M 25/0029 |
| | | | 604/528 |
| 8,241,274 | B2 | 8/2012 | Keogh et al. |
| 8,353,863 | B2 | 1/2013 | Imran |
| 8,394,050 | B2 | 3/2013 | Bardy |
| 8,961,398 | B2 | 2/2015 | Makower et al. |
| 9,226,774 | B2 | 1/2016 | Smith |
| 10,172,525 | B2 | 1/2019 | Davis et al. |
| 2002/0107559 | A1 | 8/2002 | Sanders et al. |
| 2007/0066988 | A1 | 3/2007 | Datta et al. |
| 2007/0275035 | A1 | 11/2007 | Herman et al. |
| 2009/0234273 | A1 | 9/2009 | Intoccia et al. |
| 2010/0016664 | A1 | 1/2010 | Viola |
| 2011/0275891 | A1 | 11/2011 | Shemi |
| 2012/0041534 | A1 | 2/2012 | Clere et al. |
| 2016/0038018 | A1 | 2/2016 | Wilson et al. |
| 2016/0066770 | A1 | 3/2016 | Barbato et al. |
| 2016/0166336 | A1 | 6/2016 | Razzaque et al. |
| 2017/0224986 | A1 * | 8/2017 | Imran ............... A61N 1/36007 |
| 2019/0099554 | A1 | 4/2019 | Leeflang et al. |

OTHER PUBLICATIONS

Frontiers at the Top of Citation and Impact Metrics. Frontiers, Nov. 21, 2018, blog.frontiersin.org/2018/07/02/impact-factor-scientific-academic-journal-ranking-report/. Retrieved on Aug. 3, 2020.

Tremp, Mathias, et al. "Disulfiram Implantation for the Treatment of Alcoholism: Clinical Experiences from the Plastic Surgeon's Point of View." Journal of the Korean Society of Plastic and Reconstructive Surgeons, Korean Society of Plastic and Reconstructive Surgeons, Apr. 10, 2020, www.e-aps.org/journal/view.php. Retrieved on Aug. 3, 2020.

* cited by examiner

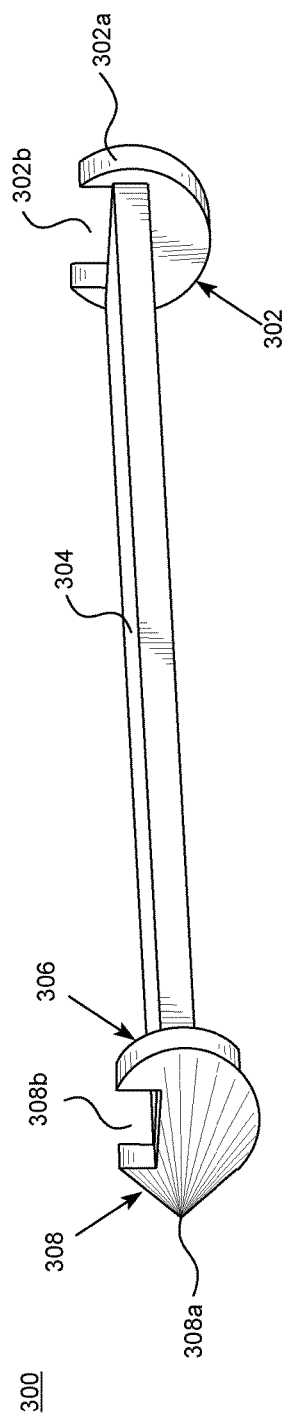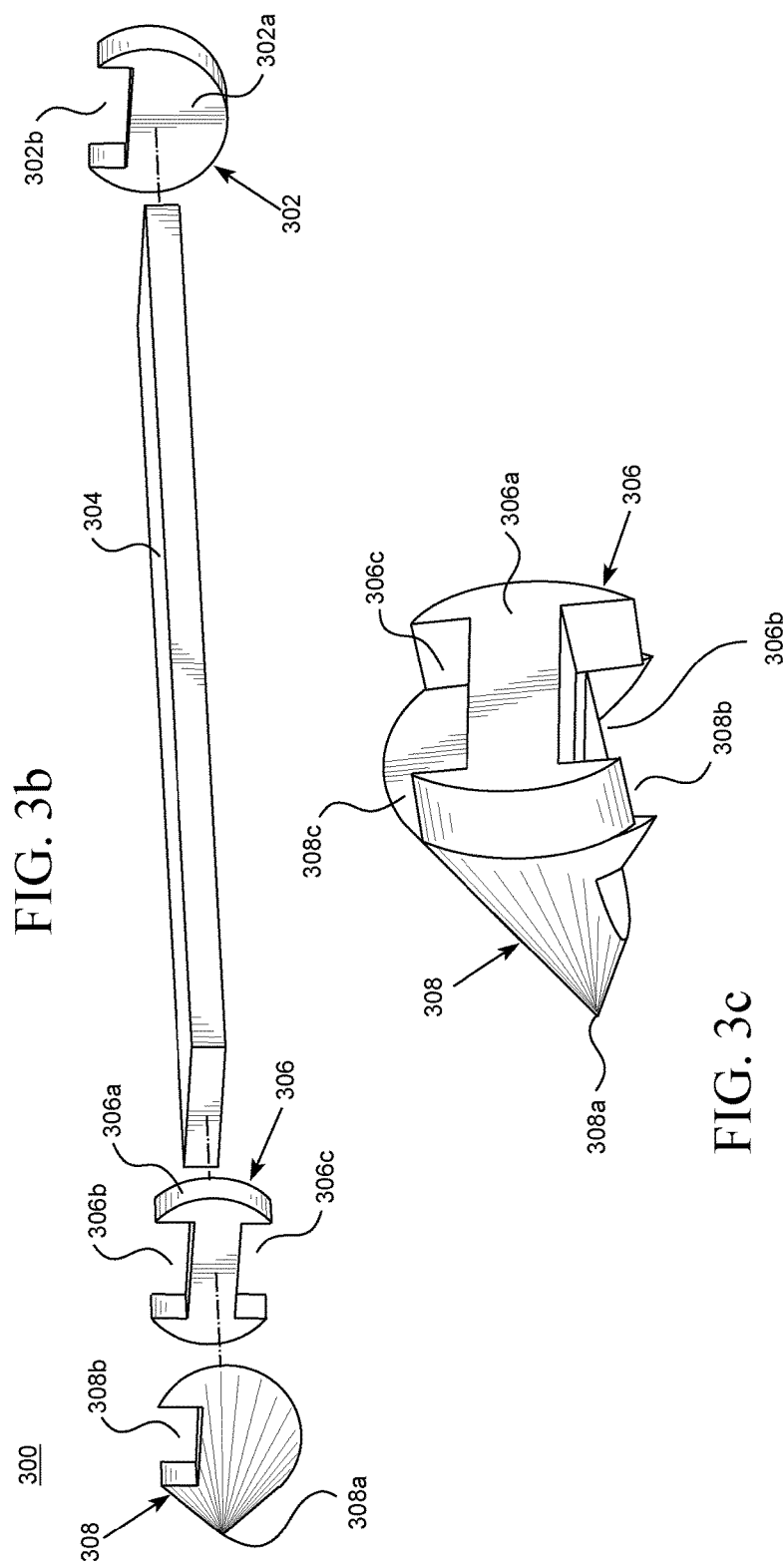

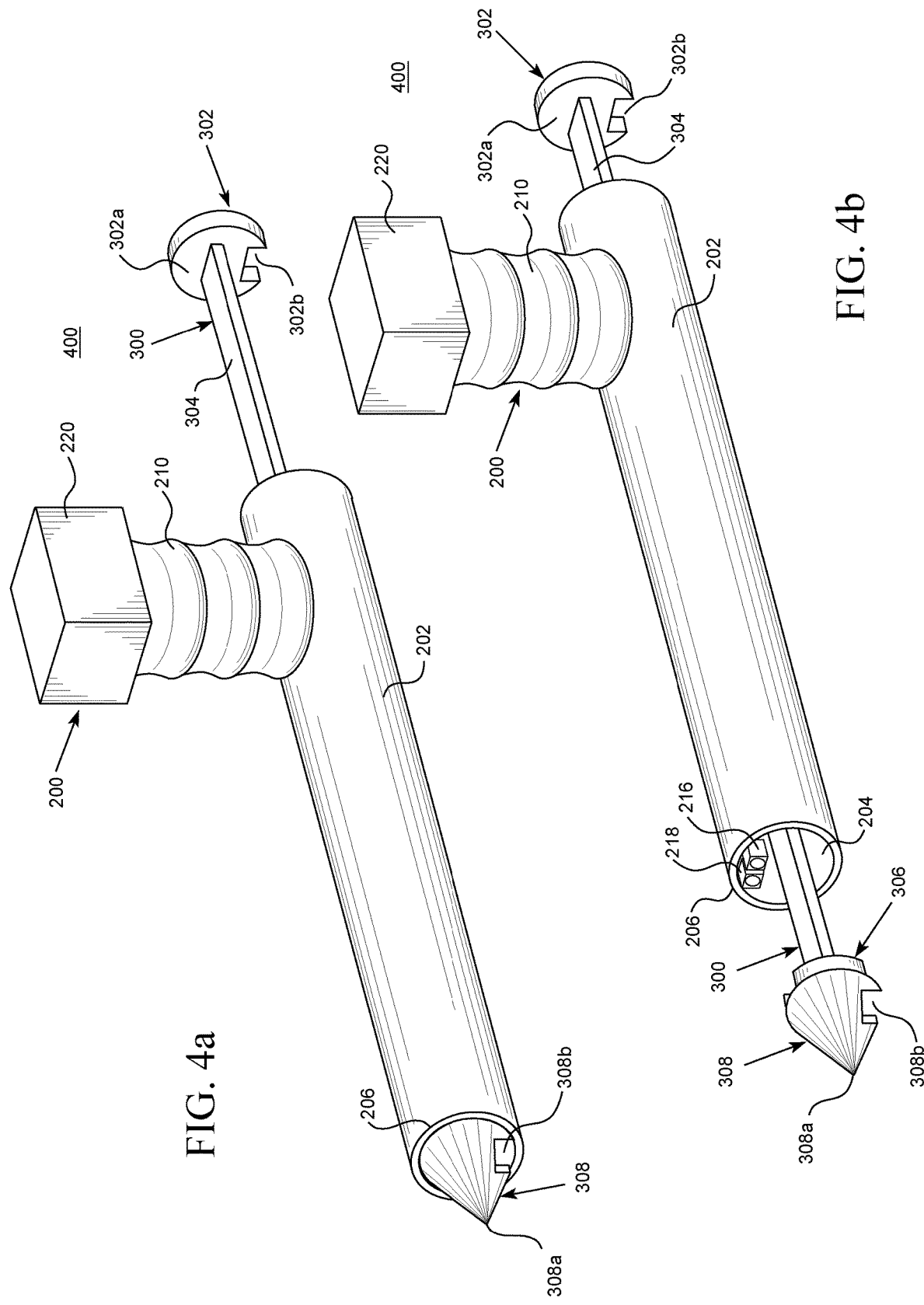

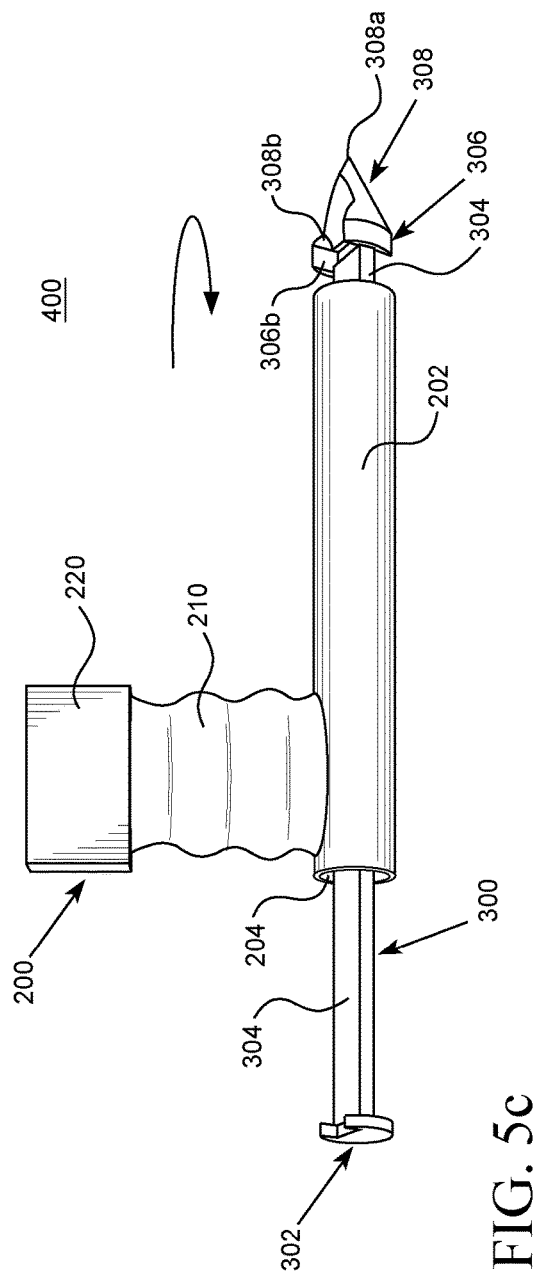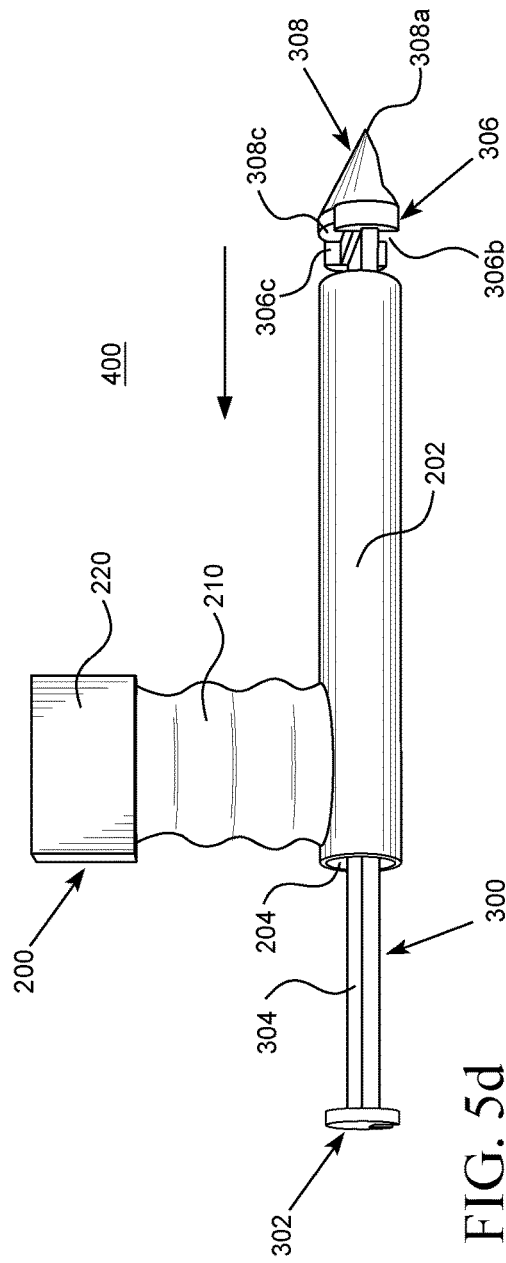
FIG. 5c
FIG. 5d

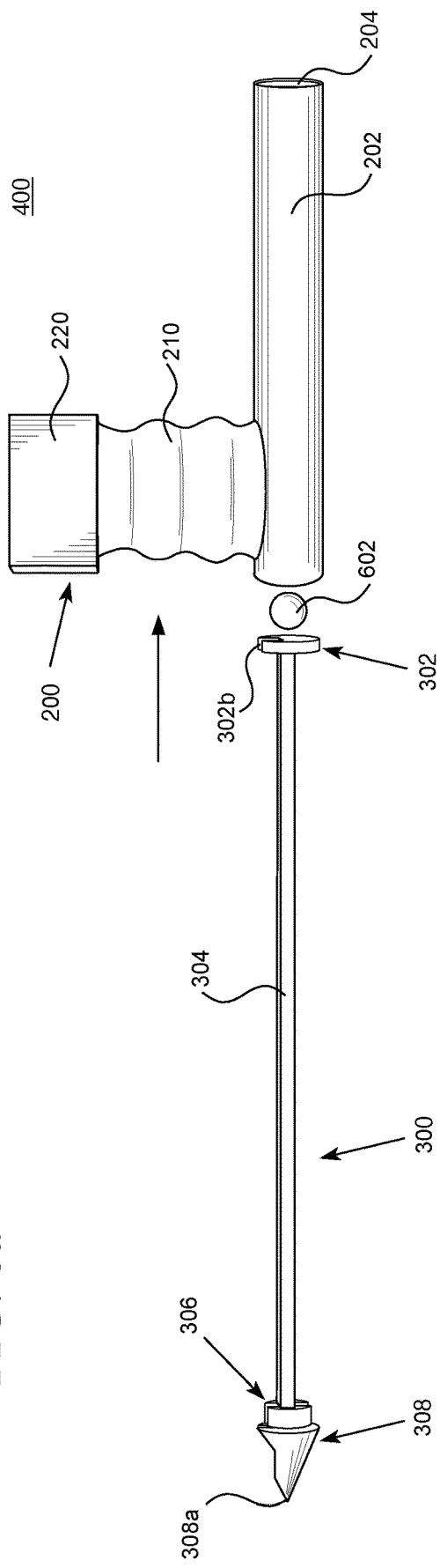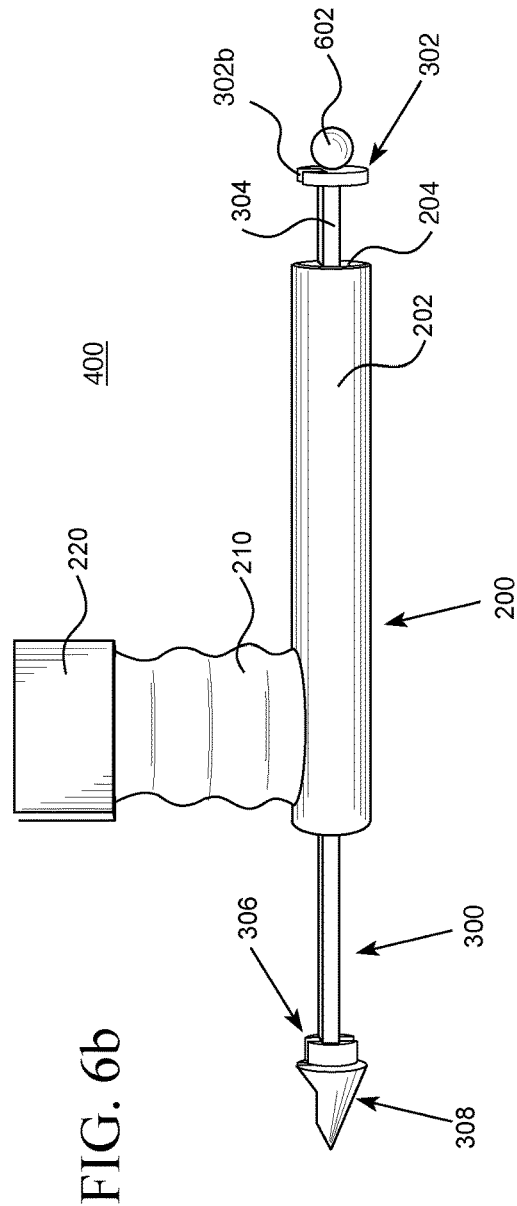
FIG. 6a
FIG. 6b

MEDICAL IMPLANT DELIVERY DEVICE

TECHNICAL FIELD

The present invention relates to medical implant delivery devices for delivering substances to targeted tissue areas of a patient.

BACKGROUND

Problem drinking that becomes severe is given the medical diagnosis of alcohol use disorder, or AUD, a chronic relapsing brain disease characterized by compulsive alcohol use, loss of control over alcohol intake, and a negative emotional state when not using. According to the National Institute on Alcohol Abuse and Alcoholism, over 15 million adults in the U.S. ages 18 and older had AUD in 2015. Global statistics on AUD are even more alarming than those of the U.S.

Currently, there is no cure for AUD. Treatment typically includes participation in mutual support groups and individual therapy, often in combination with pharmaceutical treatments. In 1949, disulfiram became the first drug approved in the U.S. for treatment of alcoholism, and it is still widely prescribed today, despite extensive research into various treatments for AUD. In general, disulfiram interferes with the metabolism of alcohol thus causing a range of unpleasant symptoms such as nausea, vomiting, fainting, rapid pulse and flushing of the skin. The anticipation of these effects can help some people avoid drinking while taking disulfiram.

Unfortunately, the effectiveness of disulfiram is often limited because, at least in the U.S., it is orally administered, and compliance among those taking it is difficult to monitor. To overcome these drawbacks, implants have been developed that are intended to release a therapeutic dose of disulfiram over an extended period of time ranging from weeks to months. Implant treatment is widely available in Europe, particularly in Eastern European countries such as Latvia, Poland, and Ukraine.

SUMMARY

Disclosed herein is a medical implant delivery device that can be used when highly accurate placement of an implant is desired. The medical implant delivery device may be beneficial when minimally invasive techniques are desired, as it is capable of providing a safe and relatively easy and simple way of implant placement. Further, it can facilitate removal of similar occurrences. The medical implant delivery device of the present disclosure is provided to penetrate body tissue during surgical procedures and to provide a simultaneous generally forward directional view of the body tissue as it is being dissected.

The medical implant delivery device comprises a handheld assembly and an obturator. The handheld assembly can include an elongated shaft defining a chamber having a distal end and a proximal end, and an imaging device secured within the chamber adjacent to the distal end. The imaging device can comprise a light source and a lens. The obturator can include an elongated member having a light transmitting member and a plunger, wherein the obturator may be slidably disposed in a first position such that at least a portion of the elongated member may be within the chamber and the light transmitting member may be optically coupled to the light source and the lens.

The obturator can be removed from the chamber and can be configured to be slidably disposed in a second position such that at least a portion of the elongated member may be within the chamber and the light transmitting member cannot be optically coupled to the light source and the lens. In some embodiments, when the device is in the first position, the light transmitting member is closer to the distal end of the elongated shaft compared to the plunger. In some embodiments, the obturator is removable from the chamber and configured to be slidably disposed in a second position such that at least a portion of the elongated member is within the chamber and the plunger is closer to the distal end of the elongated shaft compared to the light transmitting member.

A method of using the medical implant delivery device is also disclosed herein. The method includes: providing the medical implant delivery device, contacting the skin of a patient with the light transmitting member, dissecting tissue of the patient thereby forming an intramuscular pocket, removing the obturator from the device, reinserting the obturator in a second position, and delivering a medical implant within the intramuscular pocket.

A kit including the medical implant delivery device is also disclosed herein. The kit can include at least one medical implant. In some embodiments, the medical implant is a substance for treating alcohol use disorder, for example, the medical implant may include disulfiram.

Features and advantages of the invention will be more readily understood from the following detailed description which should be read in conjunction with the accompanying drawings.

DESCRIPTION OF THE DRAWINGS

The drawings, which are not necessarily to scale, are schematic illustrations and are not intended to limit the scope of the disclosure in any way. The disclosure may be more completely understood in consideration of the following description with respect to various example in connection with the accompanying drawings in which:

FIG. 2b shows a partial, cut-away perspective view of an embodiment of the handheld assembly shown in FIG. 2a;

FIG. 3a shows a perspective view of an embodiment of an obturator in accordance with the present disclosure;

FIG. 3b shows an exploded view of the obturator shown in FIG. 3a;

FIG. 3c shows a rear view of selected components of the obturator shown in FIG. 3a;

FIG. 4a shows a perspective view of the medical implant delivery device employing the components of FIGS. 2a-2b and 3a-3c;

FIG. 4b shows a perspective view of the medical implant delivery device employing the components of FIGS. 2a-2b and 3a-3c FIGS. 5a-5d show steps by which the obturator of FIGS. 3a-3c can be loaded and operated in the handheld assembly of FIGS. 2a-2b; and FIGS. 6a-6c show steps by which the medical implant delivery device of FIGS. 4a-4b can be used to deliver an exemplary implant to a desired location.

DETAILED DESCRIPTION

The types of medical implants which may be used with the device are not particularly limited and may include those intended for therapeutic or cosmetic purposes, for example, pharmaceutical medications in various solid, liquid, or gel forms. For example, the medical implant may comprise a substance for treating alcohol use disorder. In particular, the substance for treating alcohol use disorder comprises disulfiram.

The medical implant delivery device may be provided as part of a kit in which one or more medical implants are included.

In the following description, as is traditional, the term "proximal" refers to the portion of the device, assembly, or components closest to the operator, while the term "distal" refers to those remote from the operator.

Figure 1:
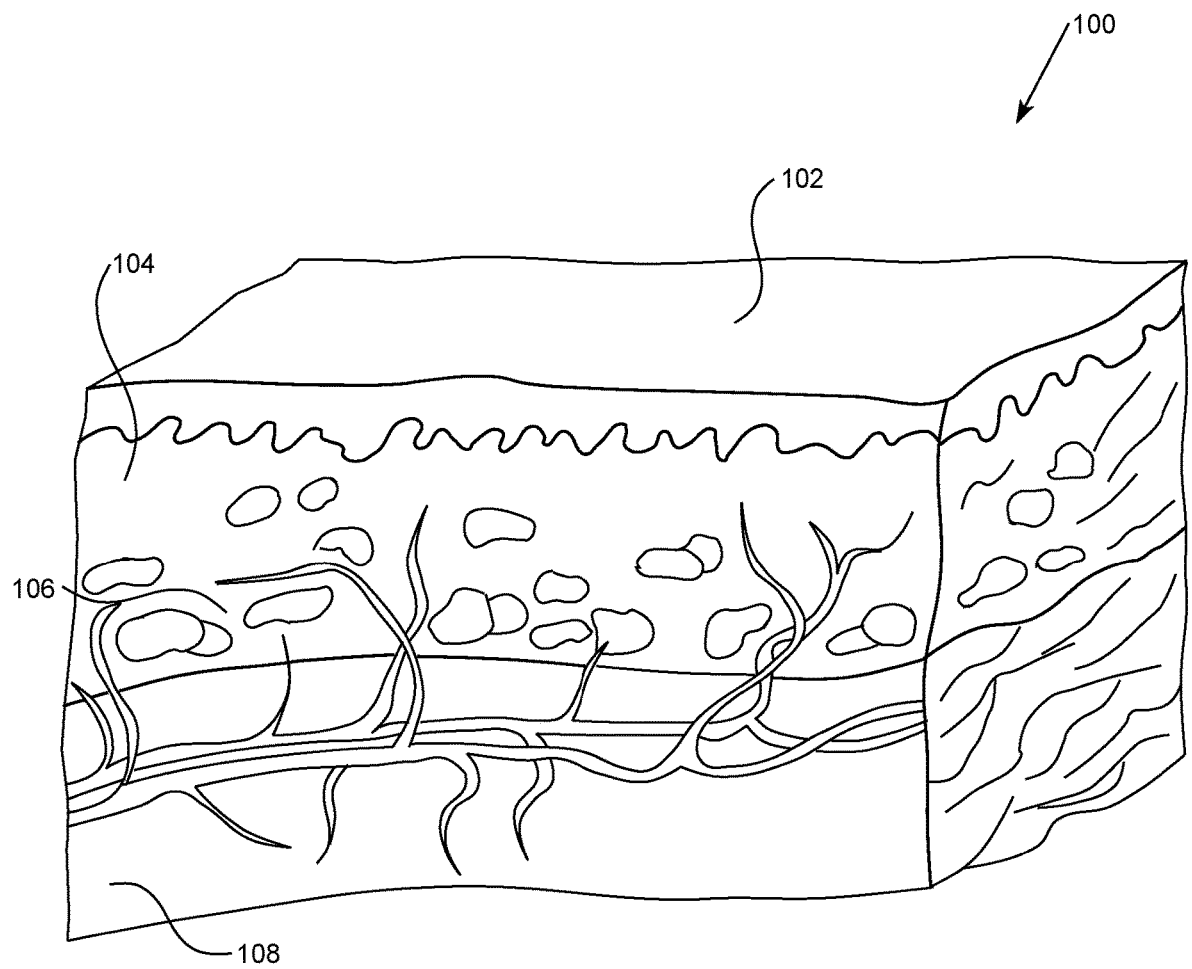
FIG. 1 is a schematic cross-sectional view of human skin.

FIG. 1 is a schematic cross-sectional view of human skin 100, showing various areas to which implants may be delivered. Below skin surface 102 is shown subdermal area 104, subcutaneous area 106, and intramuscular area 108. Intramuscular implantation of disulfiram is reported to be safer and more effective than subdermal and subcutaneous implantation, particularly when an implant is placed near an incision, which often results in inflammation, infection or extrusion.

Figure 2A:
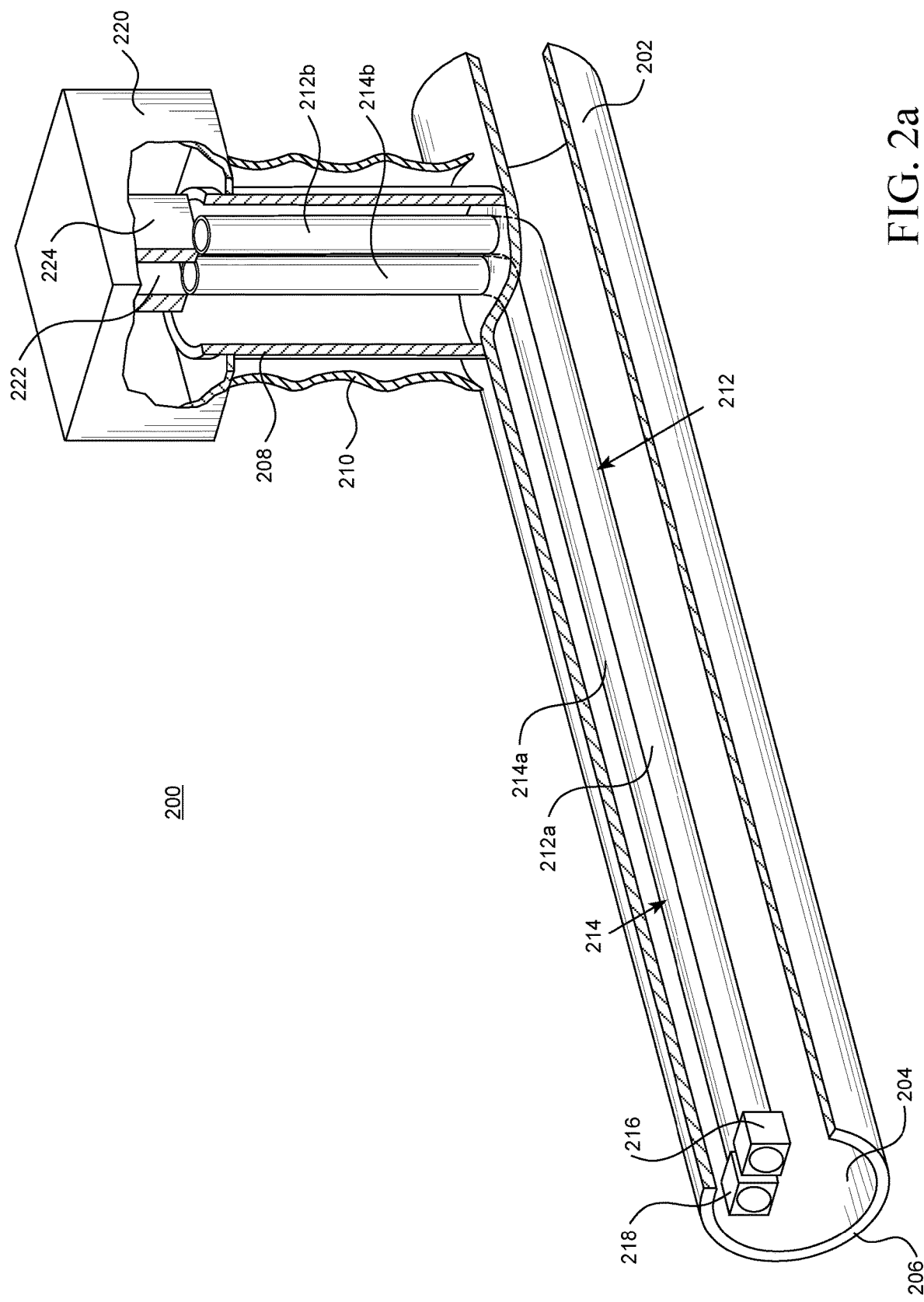
FIG. 2a shows a cut-away perspective view of an embodiment of a handheld assembly in accordance with the present disclosure.
Figure 2B:
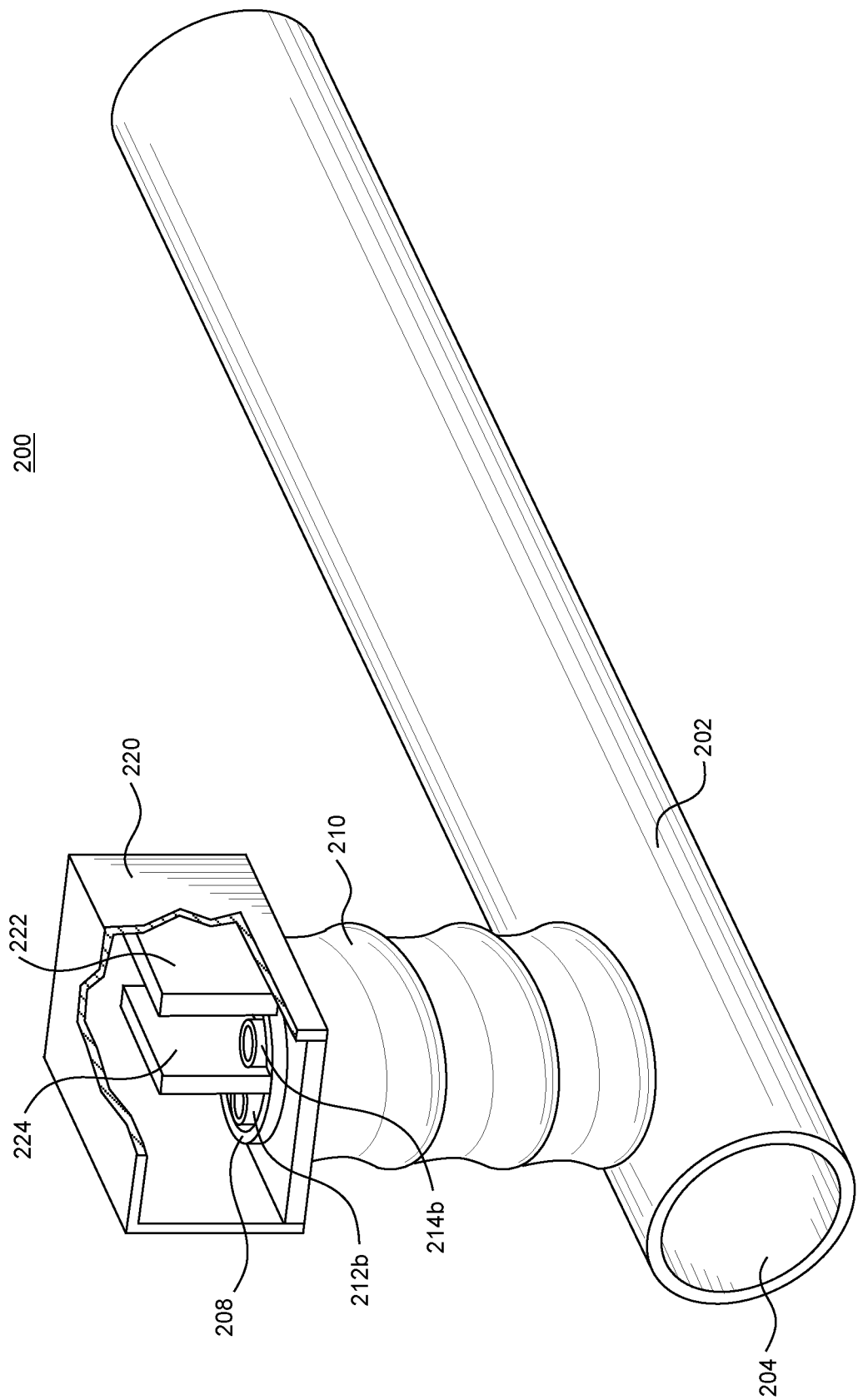

FIG. 2a illustrates, in perspective view, handheld assembly 200 of the present disclosure. Handheld assembly 200 includes elongated shaft 202, also referred to herein as first elongated shaft 202, which can define chamber 204 and have a distal end adjacent to distal edge 206. In some embodiments, elongated shaft 202 is generally cylindrical as shown in FIG. 2a, but it may have other useful shapes such as square, rectangular, triangular, elliptical, or it may be otherwise curved to facilitate necessary positioning and object placement. It is contemplated that elongated shaft 202 may have the same or different shape on the outside (as it appears in FIG. 2a) compared to the shape of chamber 204. In some embodiments, the handheld assembly may include a handle such as handle 210 attached to elongated shaft 202. Handle 210 may be adjacent or near the proximal end of elongated shaft 202 and may be smooth or have ridges, as illustrated in FIG. 2b, such that the user can ergonomically grip the device.

Secured within chamber 204 of elongated shaft 202 can be an imaging device comprising a light source and a lens. In some embodiments, the light source may be secured in a way that does not inhibit the functionality or usefulness of the assembly. The light source may be any type of light source useful for providing illumination of tissue when the assembly is being used with the obturator, as described below. For example, light emitting diodes (LEDs) are one type of light source that may be used. The imaging device may also include a lens, which may be part of a camera or video device, as described below. Positioning of the imaging device within the chamber is described below in more detail.

In the embodiment shown in FIG. 2a, the imaging device can comprise camera or video device with lens 216 and light source 218 secured within chamber 204 and near distal edge 206 of the chamber. Conduits 212 and 214 may be attached to the lens and light source, respectively, to serve as protective coverings for the wiring used to power the imaging device. In general, wiring connected to the imaging device can be secured within the chamber in such a way that does not inhibit the functionality or usefulness of the assembly. In general, one or more conduits may or may not be used, depending upon the particular design and use of the assembly.

In the embodiment shown in FIG. 2a, conduit 212 can include horizontal section 212a, which can extend along the upper portion of chamber 204 and curve around and into handle 210, and vertical section 212b which can extend the length or nearly the length of handle 210. Similarly, conduit 214 can include horizontal section 214a, which can extend along the upper portion of chamber 204, and vertical section 214b, which can extend the length or nearly the length of handle 210. For embodiments in which a handle is present, the handheld assembly may include a second elongated shaft disposed inside the handle. Second elongated shaft 208 can be included in exemplary handheld assembly 200 for provided support to the built-in conduits, as illustrated in FIG. 2b.

The medical implant delivery device can include an obturator in addition to the handheld assembly. In general, the obturator may be a probe or dissector in which an elongated member has a light transmitting member and a plunger. The obturator may be a single piece, i.e., a single piece molded or cut from a single piece of material, as described below. For embodiments in which the obturator is a single piece, the material can comprise a light transmitting material because the obturator comprises a light transmitting member. The end of the obturator may be light transmitting as long as light can be transmitted through it. The light transmitting member can be optically coupled to the light source and the lens of the imaging device such that light emitted from the light source can enter the light transmitting member and be subsequently emitted therefrom. In some embodiments, the light transmitting member is a lens such that light is emitted in one or more predetermined directions. In some embodiments, the light transmitting member is not a lens such that light is emitted diffusively.

In some embodiments, the light transmitting member is designed and configured to dissect tissue of a patient. In this case, the light transmitting member may have a sharp or blunt tip, or it may have blade-like features.

The plunger of the obturator can be designed and configured such that the obturator can be used to deliver an implant to a desired location within the tissue of a patient.

In some embodiments, the light transmitting member and/or the plunger may have one or more cutaways, cutouts, or slots such that the obturator may be used in conjunction with the handheld assembly as described further below.

FIGS. 3a-3c show perspective views of an embodiment of the obturator in accordance with the present disclosure. Obturator 300 comprises light transmitting member 308 attached to elongated member 304 by adapter 306. Obturator further comprises plunger 302 having plunger body 302a and cutaway 302b. Plunger 302 can be attached to an end of elongated member 304 opposite that of light transmitting member 308. In some embodiments, elongated member 304, adapter 306, and optionally plunger 302 can be a single piece molded or cut from a single material, and light transmitting member 308 is a separate piece attached to the adapter.

FIGS. 4a-4b show perspective views of medical implant delivery device 400 comprising handheld assembly 200 and obturator 300. In FIG. 4a, obturator 300 is slidably disposed in a first position such that at least a portion of the elongated member is within chamber of elongated shaft 202 and light transmitting end 308a is optically coupled to the light source and the lens. In the first position, light transmitting end 308a may be closer to the distal end of elongated shaft 202 compared to plunger 302. As illustrated in FIGS. 4a-4b, elongated member 304 can be longer than elongated shaft 202. FIG. 4b illustrates obturator 300 in a more forward position relative to the first position shown in FIG. 4a.

Figure 5A:
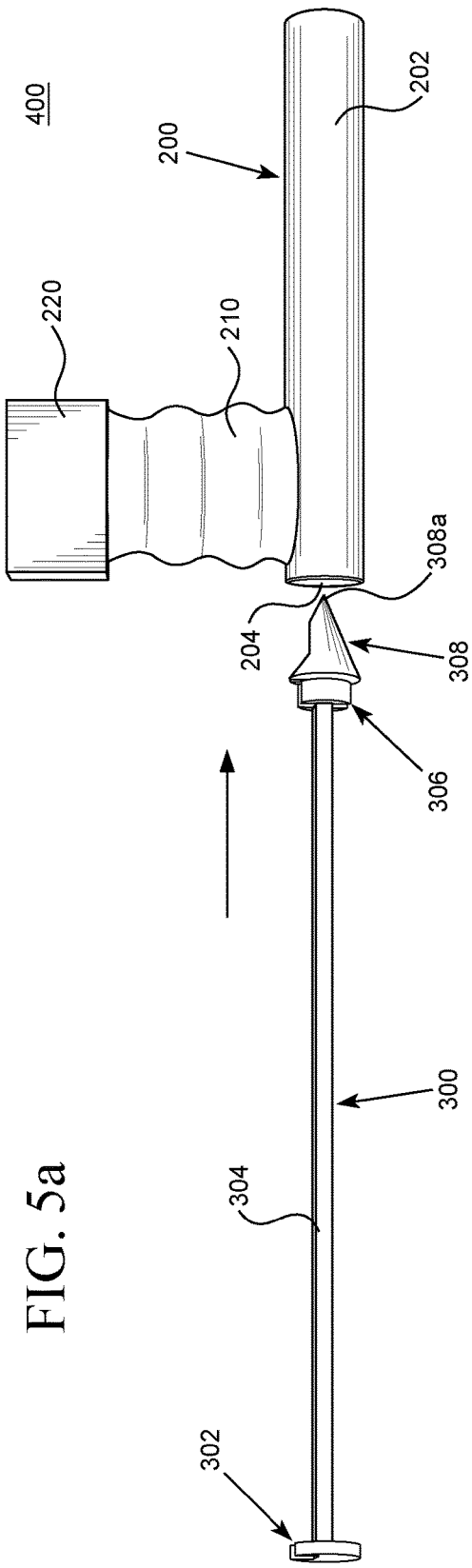
Figure 5B:
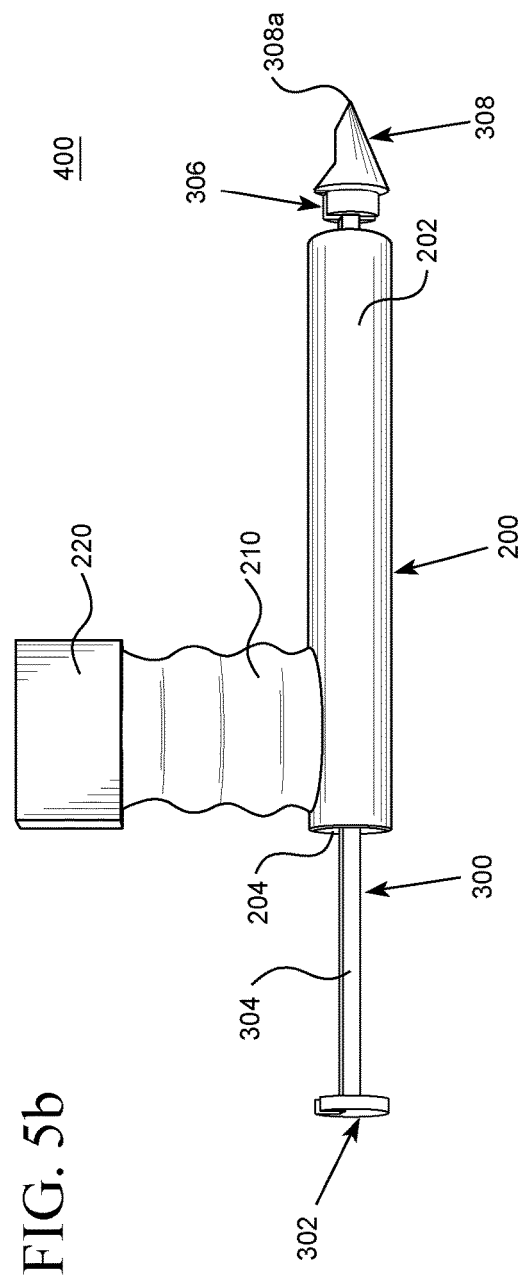

FIGS. 5a-5d show steps by which obturator 300 can be loaded in handheld assembly 200. In this embodiment of medical implant delivery device 400, elongated shaft 202 defines a first longitudinal axis along a length of shaft, elongated member 304 defines a second longitudinal axis along a length of the elongated member, and the first and second longitudinal axes are parallel to each other. In FIG. 5a, obturator 300 is inserted into the chamber of elongated shaft 202, as indicated by the arrow, with light transmitting end 308a in a forward position relative to plunger 302. In FIG. 5b, obturator 300 is pushed or slid forward enough such that light emitting member 308 extends beyond the distal end of elongated shaft 202, a movement that is possible because of cutaway 306b of adapter 306 and cutaway 308b of the light emitting member. Without these two cutaways, the conduits would obstruct obturator 300 from being inserted into chamber 204 of elongated shaft 202 to obtain the position shown in FIG. 5b. Cutaway 302b of plunger 302 can be oriented in the same way as cutaways 306b and 308b.

FIG. 5c shows an arrow indicating obturator 300 being rotated, either clockwise or counterclockwise, by about 180 degrees. The resulting orientation of obturator 300 with respect to handheld assembly 200 is shown in FIG. 5d wherein the combination of cutaway 308b and cutaway 306b is now at the bottom of chamber 204, and cutaway 306c of adapter 306 in combination with face 308c of light transmitting member 308 are generally in front of the imaging device comprising light source 218 and lens 216. Obturator 300 can then be pulled back as indicated by the arrow in FIG. 5d, until light transmitting member 308 is optically coupled to light source 218 and lens 216 to obtain first position shown in FIG. 4a. Cutaway 302b of plunger 302 can be oriented at the bottom of the chamber along with cutaways 306b and 308b.

In the method of using medical implant delivery device 400 comprising handheld assembly 200 and obturator 300, the obturator can first be loaded into the handheld assembly, as shown in FIG. 5a. When the medical implant delivery device is moved into the first position, as shown in FIG. 4a, the skin of a patient may be contacted by light transmitting member 308. Tissue of a patient can then be dissected by light transmitting member 308 to form an operative space, preferable in intramuscular area 108, depicted in FIG. 1, by movement of obturator 300 as illustrated in FIGS. 4b and 5b-5c, wherein the obturator is rotated to create the pocket of operative space. Obturator 300 can then be removed from the patient, leaving the pocket of operative space. The imaging device in cooperation with obturator 300 can provide simultaneous visualization during dissection of tissue until the operative space is created.

Figure 6C:
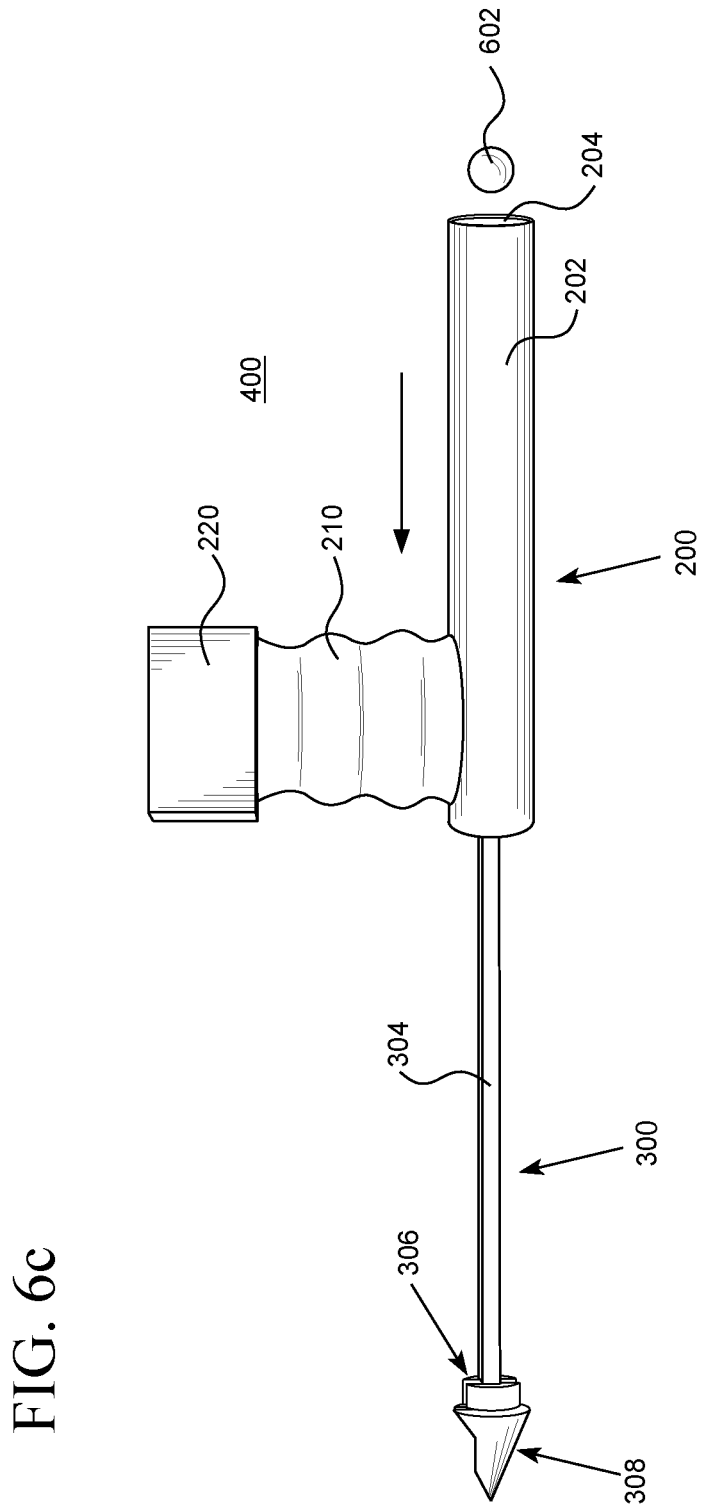

The next step in the method of using medical implant delivering device 400 comprising handheld assembly 200 and obturator 300, is shown in FIGS. 6a-6c. Obturator 300 can be removed from handheld assembly 200 and rotated around in the plane of elongated member 304 such that plunger 302 may be closer to the distal end of elongated shaft 202 compared to light transmitting member 308 and with cutaway 302b of the plunger in a topmost position. This configuration may be referred to herein as the second position. In FIG. 6a, obturator 300 is inserted into chamber 204 of shaft 202, as indicated by the arrow, with plunger 302 in a forward position relative to light transmitting member 308. Medical implant 602, which can be, for example, a disulfiram implant, can then be aligned with elongated shaft 202 and plunger 302. The resulting medical delivery device can then be put in contact with a patient, preferably in a location where the operative space has been created. Obturator 300 can then be pushed or slid in a forward directed as shown in FIG. 6b such that plunger 302 extends near the distal end of shaft 202 and delivers medical implant 602 to a target area beneath the skin, preferably within the intramuscular pocket created using light transmitting member 308 as described above. Once medical implant 602 is in the intramuscular pocket, obturator 300 can be pulled back as indicated by arrow in FIG. 6c, and the medical implant can remain in the intramuscular pocket.

In general, as described above, the shape of the chamber of the elongated shaft is not particularly limited, and likewise for the overall shape of the obturator. Any combination of shapes may be used, as long as the medical implant delivery device can be used as desired. For the embodiment described above, the shape of chamber 202 is generally cylindrical and obturator 300 is generally cylindrical such that it can be rotated when it is in the first position illustrated in FIG. 5c and, optionally, the second position illustrated in FIG. 6b.

In some embodiments, for example, the embodiment described above, particular dimensions of the handheld assembly and the obturator may be useful. For example, the elongated shaft of the handheld assembly may have a length of from about 8 to about 10 centimeters or from about 10 to about 16 centimeters, and it may have a diameter of from about 10 to about 18 millimeters. The handle, if present, may have any useful dimensions that enable an ergonomic grip on the device by a user. As shown in FIG. 2a, the handle assembly may comprise housing 220 attached to an upper portion of handle 210, particularly for housing electrical components needed to power the light source and camera/video means as described further below. The size and weight of the housing and electrical components may affect the overall design of the handheld assembly as is typically the case with handheld instruments.

Dimensions and shapes of the obturator are not particularly limited, provided the medical image delivery device can function as desired. In general, the elongated member of the obturator may be longer than the elongated shaft of the handle assembly such that a surgeon can manipulate the position of the obturator as it is slid back and forth in the chamber. For example, if the length of the elongated shaft is from about 10 to about 16 cm, then it may be useful for the length of the elongated member to be about 20 cm.

Dimensions of the light transmitting member are not particularly limited, provided the medical implant delivery device can function as desired. For example, if the medical implant delivery device is being used to deliver an implant to a targeted tissue region of a patient, the length of the light transmitting member that extends out from the distal end of the chamber can be long enough to reach the necessary depth (as measured from the distal end of the chamber). For another example, if the medical implant delivery device is being used to deliver an implant to an intramuscular region of a patient, the length of the light transmitting member that extends out from the distal end of the chamber may be at least as long as the distance measured from the distal end of the chamber to the particular intramuscular area, wherein the chamber does not reach further than subcutaneous area 106. For yet another example, if the medical implant delivery device is being used to deliver an implant to an intramuscular region of a patient, the length of the light transmitting member may be from about 1 to about 3 cm.

The handle assembly and obturator can be manufactured using any suitable material as long as the components can function as desired. In general, the handle assembly and obturator can be made from either thermoplastic or thermoset polymeric materials such as Lucite® from Lucite International, ceramic materials, metals or alloys such as stainless steel, titanium and the like. These components may be molded or cut to desired specifications. The handle assembly and obturator may be comprised of materials that can withstand sterilization through heat or radiation or other means. In these cases, the medical implant delivery device may be designed and configured such that the electrical and optical components can be temporarily removed. One or more components of the medical implant delivery device may be designed to be reusable or may be intended for single use.

As mentioned above, the imaging device can include a lens, and the lens may be part of a camera device configured to provide still photos and/or video as desired by the surgeon. The lens may be mounted such that it overlies an image sensor and can focus light entering the lens onto a photosensitive area of the image sensor. An integrated lens can be made by bonding the lens assembly onto an image sensor chip by means of an optically inert glue. The camera can further comprise any type of camera used in the medical industry; generally, those used for surgery and diagnostic applications. The camera can comprise an endoscope camera or microcamera with any size lens diameter, as long as the desired field of illumination is obtained. For example, the camera can comprise a microcamera with a 4 mm lens. Particularly useful microcameras can provide a resolution of at least about 1024 pixels/per inch when used in combination with an appropriate image sensor as described below.

The image sensor can convert light incident on the photosensitive semiconductor elements into electrical signals. The signals from the sensor can be digitized and used to reproduce the image that was incident on the sensor. Two types of image sensors are Charge Coupled Devices (CCD) and Complementary Metal Oxide Semiconductor (CMOS) camera chips. The image data captured by the image sensor can then be decoded by the signal processing integrated circuit (IC). The variety of image sensor output formats and video signal processing ICs is well documented and understood in the consumer electronics industry, and so this process is not explained in further detail. Once the signal has been converted to a suitable format, it can be transferred to an external control box as described below.

Electrical wiring from the imaging device/lens and light source can be carried through the conduits and can be routed to electrical connections within the housing. The electrical wiring may include power, data/signal, and control lines. Power and control commands can be received through the respective wires or ribbon electrical conduits from the control box, and the data/signal line can carry the video and/or photo images to the control box. The control box may be one or more digital phones, digital pads, computers, etc.

Included in housing 220 can be a power management integrated circuit (IC), a clock or crystal, and a signal processing IC, as well as an IC for digital input and output. Electrical wiring can connect the printed circuit board (PCB) 224 to the image sensor or lens and light source. Power to the light source can be routed via a power management circuit on the camera PCB. Controlling circuitry for adjusting the intensity of the light may be included in the camera PCB. This can be achieved by using a device such as an LED driver, which can be controlled via the same or separate control line depending on the control technique employed.

The external control box can transmit power and control commands from its internal circuitry to the camera and lens and can serve to process and retransmit the photos/video streams received from the camera to a display device, such as an LCD display on the control box or a video monitor connected to video output connectors on the control box. The control box can comprise an image and signal processing circuitry in an enclosure with a control panel, LCD display, and connectors. The LCD display in conjunction with a control panel can provide a menu-driven interface.

The control box can comprise image and signal processing ICs, a crystal or clock, input and output interfaces, a power management IC, button input switches, and a controller CPU. After the control box receives the signal from the camera, the controller CPU, which can include a signal processing IC, can decode the signal and send it to image processing circuits. These circuits can process the photo/video signal in order to enhance image quality, extract still images, and convert the photo/video format to other output formats. Once the photo/video images have been processed, they can be sent back to the controller CPU for output to an external monitor.

The controller CPU can also interface with an image sensor of the camera, which can allow users to employ the controls such as a menu-driven interface to control mode settings, brightness, and exposure time by writing digital commands to specific registers controlling each of these parameters on the image sensor of the camera. These registers can be addressed by their unique addresses, and digital commands can be read from and written to these registers to change the different parameters.

Fiber optic bundles may be employed to transfer images to the imaging sensor. The imaging sensor can receive the light signals and digitize them for transfer to a photo/video processing system and for display on a monitor or other output. In some embodiments, the imaging device may not utilize an LED as a light source but may instead employ one or more fiber optic bundles to provide illumination of the surgical field and possibly use for heat sterilization. The fiber optic bundle can interface against a microcamera located within the handle rather than the end of the device.

In some embodiments, electrical/communication wires may not be connected to the housing. Instead, imaging device may transmit data directly to an external control box by using a wireless protocol such as Bluetooth. A small battery can be included in the housing in order to power the electrical components, A wireless transceiver, which may be responsible for transmitting the data at a given frequency, can be found both in the camera capsule PCB and circuitry of the external control box. Wireless transmission of video images during surgical procedure can be provided by the integrated PCB.

In other embodiments, an external control box can include PC connectivity. Video and still images can be stored onto internal memory. These images can then be transferred to external removable flash memory or transferred directly to a PC via serial communication protocols such as Universal Serial Bus (USB). Other interface standards such as High Definition Multimedia Interface (HDMI) and Video Graphics Array (VGA) may be used.

The storage of images in memory and serial communication protocols such as USB are well documented and understood in the consumer electronics industry and so they will not be explained in further detail. Such an embodiment facilitates the inclusion of these video or still images in a patients electronic medical record (EMR) by transferring the images to a personal computer. In addition, the image processing capabilities of the control box can convert the image and video data to a compatible format such as jpeg, mpeg, or others for filing in the patient's EMR. Furthermore, data can be retained in the control box for a duration of time by assigning a unique identifier to the corresponding images of each surgical procedure.

While embodiments of the invention have been illustrated and described, it will also be apparent that various modifications can be made without departing from the scope of the invention. It is also contemplated that various combinations or subcombinations of the specific features and aspects of the disclosed embodiments can be combined with or substituted for one another in order to form varying modes of the invention. Accordingly, it is not intended that the invention be limited, except as by the appended claims.

What is claimed is:

1. A medical implant delivery device comprising:
   a handheld assembly comprising:
      an elongated shaft defining a chamber having a distal end and a proximal end, and
      an imaging device secured within the chamber adjacent to the distal end, the imaging device comprising a light source and a lens; and
   a reversible obturator comprising:
      an elongated member having a light transmitting member on a first end and a plunger on a second, opposite end,
      wherein, in a first position, the reversible obturator is slidably disposed within the chamber such that the light transmitting member is positioned to be optically coupled to the light source and the lens, and the plunger is positioned externally to the chamber, and
      wherein, in a second position, the positions of the obturator and plunger are reversed.

2. The medical implant delivery device of claim 1, wherein
   an entirety of the reversible obturator is completely removable from the chamber and configured to be slidably disposed in the second position, and
   in the second position, at least a portion of the elongated member is within the chamber and the light transmitting member is not optically coupled to the light source and the lens.

3. The medical implant delivery device of claim 1, wherein, in the first position, the light transmitting member is closer to the distal end of the elongated shaft compared to the plunger.

4. The medical implant delivery device of claim 3, wherein
   an entirety of the reversible obturator is completely removable from the chamber and configured to be slidably disposed in the second position, and
   in the second position, the positions of the plunger and the light transmitting member are reversible such that the plunger is closer to the distal end of the elongated shaft compared to the light transmitting member.

5. The medical implant delivery device of claim 1, wherein
   the elongated shaft defines a first longitudinal axis along a length of shaft,
   the elongated member defines a second longitudinal axis, and
   the first and second longitudinal axes are parallel to each other when the device is in the first and second positions.

6. The medical implant delivery device of claim 1, wherein the light transmitting member is configured to dissect tissue of a patient.

7. The medical implant delivery device of claim 1, wherein the light transmitting member includes a lens.

8. The medical implant delivery device of claim 1, wherein the light transmitting member comprises a tip that is from about 1 cm to about 3 cm from the distal end of the elongated shaft when the device is in the first position.

9. The medical implant delivery device of claim 3, wherein the elongated shaft is generally cylindrical and the obturator is configured to be rotated when in the first position.

10. The medical implant delivery device of claim 1, further comprising:
    a first set of one or more markings on the handheld assembly; and
    a second set of one or more markings on the obturator,
    wherein the one or more markings of the first set are matchable to the one or more markings of the second set, indicating the distance between an end of the obturator and an end of the elongated shaft.

11. The medical implant delivery device of claim 1, the device further comprising:
    a handle attached to the elongated shaft and adjacent the proximal end of the shaft, and
    a housing attached to the handle,
    wherein the housing contains one or more electronic components.

12. The medical implant delivery device of claim 1, wherein the device is wireless.

13. The medical implant delivery device of claim 1 in combination with at least one medical implant, wherein the medical implant comprises disulfiram or any other substance for treating alcohol use disorder.

14. The medical implant delivery device of claim 1, wherein the light transmitting member and the plunger include cutouts that are aligned and enable passage of the light transmitting member and the plunger past the light source and the lens of the imaging device.

15. The medical implant delivery device of claim 1, further comprising an adapter positioned adjacent to the light transmitting member.

16. The medical implant delivery device of claim 15, wherein both the light transmitting member and the adapter include cutouts that are aligned and enable the light transmitting member and the adapter to slide past the light source and the lens.

17. The medical implant delivery device of claim 16, wherein
    the plunger is approximately disc shaped, and
    the plunger includes a cutout that aligns with the cutouts on the light transmitting member and the adapter.

18. The medical implant delivery device of claim 1, wherein rotation of the light transmitting member causes the light source to couple to the light transmitting member.

* * * * *